(12) United States Patent
Santos et al.

(10) Patent No.: US 9,937,470 B2
(45) Date of Patent: Apr. 10, 2018

(54) PRODUCTION OF NEAR MONODISPERSE PARTICLES USING MILLING AND MEMBRANE SEPARATION

(71) Applicant: Hovione International Ltd, Wanchai, Hong Kong (HK)

(72) Inventors: Jośe Luis Santos, Ericeira (PT); Filipe Gaspar, Oeiras (PT)

(73) Assignee: Hovione International Ltd, Wanchai, Hong Kong (CN)

( * ) Notice: Subject to any disclaimer, the term of this patent is extended or adjusted under 35 U.S.C. 154(b) by 770 days.

(21) Appl. No.: 14/389,117

(22) PCT Filed: Mar. 28, 2013

(86) PCT No.: PCT/GB2013/000146
§ 371 (c)(1),
(2) Date: Sep. 29, 2014

(87) PCT Pub. No.: WO2013/144554
PCT Pub. Date: Oct. 3, 2013

(65) Prior Publication Data
US 2015/0060581 A1    Mar. 5, 2015

(30) Foreign Application Priority Data
Mar. 30, 2012 (PT) .................................. 106237

(51) Int. Cl.
*A61K 9/14* (2006.01)
*B01D 61/16* (2006.01)
(Continued)

(52) U.S. Cl.
CPC ............... *B01D 61/16* (2013.01); *A61K 9/10* (2013.01); *A61K 9/14* (2013.01); *B01D 61/142* (2013.01);
(Continued)

(58) Field of Classification Search
CPC ............... B01J 2/06; A61K 9/14; B01D 61/14
See application file for complete search history.

(56) References Cited

U.S. PATENT DOCUMENTS 8,764,992 B2    7/2014   Wursche et al.
2004/0118007 A1    6/2004   Chickering, III et al.
(Continued)

FOREIGN PATENT DOCUMENTS

CN    101433786 A    5/2009
EP    1277787 A1    1/2003
(Continued)

OTHER PUBLICATIONS

Chinese 3rd Office Action, Application No. CN201380022846.9, dated Mar. 22, 2017.
(Continued)

*Primary Examiner* — Carlos A Azpuru
(74) *Attorney, Agent, or Firm* — MacMillan, Sobanski & Todd, LLC

(57) ABSTRACT

The present invention provides a method for producing particles having a reduced particle size distribution, which method comprises the steps of: a) providing a composition comprising particles; b) subjecting the particles in said composition to a size reduction step or to a size growth step; c) feeding said particles to a first membrane separation system to separate said particles according to size; d) recycling those particles that do not meet the size criteria back to step a); e) optionally, collecting in a collection tank the permeate of the first membrane separation system. Particles obtainable according to the method of the invention and characterized by having a near monodisperse particle size distribution are also provided. The particles are preferably characterized by having a particle size distribution with a span of less than 2.0. The invention also provides pharmaceutical compositions comprising particles according to (Continued)

the invention, and also apparatus for carrying out the method of the invention.

26 Claims, 1 Drawing Sheet

(51) Int. Cl.
    *B01J 2/06*     (2006.01)
    *B01D 61/14*     (2006.01)
    *A61K 9/10*     (2006.01)
    *B01D 61/18*     (2006.01)
    *B01D 63/08*     (2006.01)
    *B02C 23/08*     (2006.01)
    *B02C 23/18*     (2006.01)
    *B03B 7/00*     (2006.01)
    *B07B 1/00*     (2006.01)

(52) U.S. Cl.
    CPC ............ *B01D 61/147* (2013.01); *B01D 61/18* (2013.01); *B01D 63/08* (2013.01); *B01J 2/06* (2013.01); *B02C 23/08* (2013.01); *B02C 23/18* (2013.01); *B03B 7/00* (2013.01); *B07B 1/00* (2013.01); *B01D 2311/25* (2013.01); *B01D 2311/26* (2013.01); *B01D 2317/025* (2013.01)

(56) References Cited

U.S. PATENT DOCUMENTS

| | | |
|---|---|---|
| 2006/0008498 A1 | 1/2006 | Chen |
| 2008/0145431 A1 | 6/2008 | Nomura et al. |
| 2009/0136757 A1* | 5/2009 | Wursche ............... B01D 61/142 428/402 |
| 2010/0172994 A1 | 7/2010 | Sigmund et al. |
| 2011/0114745 A1 | 5/2011 | Buisson et al. |

FOREIGN PATENT DOCUMENTS

| | | |
|---|---|---|
| EP | 1834624 A1 | 9/2007 |
| EP | 2143423 A1 | 1/2010 |
| JP | 2009119461 A | 6/2009 |
| WO | 1999011243 A1 | 3/1999 |
| WO | 2005/053851 A1 | 6/2005 |
| WO | 2011/131947 A2 | 10/2011 |
| WO | 2013144554 A1 | 10/2013 |

OTHER PUBLICATIONS

Keck et al., "Drug nanocrystals of poorly soluble drugs produced by high pressure homogenization", European Journal of Pharmaceutics and Biopharmaceutices, 2006, vol. 62, No. 1, pp. 3-16, Abstract Only.

Kesisoglou et al., "Nanosizing—Oral formulation development and biopharmaceutical evaluation", Advanced Drug Delivery Reviews, 2007, vol. 59, No. 7, pp. 631-644, Abstract Only.

European Research Report Request for Provisional Patent No. 106237 dated Oct. 10, 2014.

International Search Report and the Written Opinion, Application No. PCT/GB2013/000146 filed Mar. 28, 2013, dated Jul. 18, 2013.

International Preliminary Report on Patentability, Application No. PCT/GB2013/000146 filed Mar. 28, 2013, dated Sep. 4, 2014.

Israeli Office Action, Application No. 234918 dated Apr. 19, 2018.

Israeli Office Action, Application No. IL 234918, dated Mar. 23, 2017.

Japanese Second Office Action, Application No. JP 2015-502436, dated Jun. 27, 2017.

Taiwanese Office Action, Application No. 102111579 dated Mar. 14, 2016.

Japanese Office Action, Application No. JP 2015-502436 dated Jan. 11, 2017.

* cited by examiner

PRODUCTION OF NEAR MONODISPERSE PARTICLES USING MILLING AND MEMBRANE SEPARATION

The present invention claims the benefit of the PCT/GB2013/000146 filed 28 Mar. 2013, which claims priority to Ser. PT/105237 filed 30 Mar. 2012.

The present invention is in the technical field of particle size reduction and classification methods. More particularly, the present invention is in the technical field of wet milling particle size reduction methods applied particularly, but not exclusively, to active pharmaceutical ingredients (APIs), drug product intermediates, excipients and drug products in combination with a size classification method using membrane technology.

The precise control of the particle size distribution of pharmaceutical materials is of critical importance. From manufacturing to stability, from delivery to efficacy, modifying the particle size may lead to changes in product attributes which enhance the behavior, activity or effectiveness of drug products. A product may be modified to be easier to be manufactured by improving its flow properties, or may become more soluble and be better absorbed in the body. As an inhalation product, it may become better dispersed and more efficiently deposited in the nose or lung. All of these benefits may be achieved by varying the particle size of the active pharmaceutical ingredient, or of the drug product intermediates, or of the excipients used or of the drug product itself. In certain cases, the beneficial effect will be achieved by increasing the particle size, in others, by decreasing it.

At the product development stage, it is important that the target particle size distribution, expressed in terms of particle size distribution data such as the median particle size be achieved with high precision, such that its variability may be contained within the limits of $\pm 5$ μm, or narrower limits, such as $\pm 1$ μm or $\pm 0.1$ μm or even $\pm 0.01$ μm.

At the industrial stage, it is important that the particle size achieved in development targeting a precise distribution be reproduced with low variability from batch to batch. In other words, there is a need for a technology which is able to place the particle size distribution exactly where it is needed and to do so reliably in development and industrial settings.

The current art comprises several techniques to modify, and particularly to reduce particle size, such as jet mill micronization and ball milling, methods which typically are conducted using dry powders, but in the case of the latter can also use liquid media. In the latter case, the suspended and processed particles may then be dried using a known method to obtain a powder. However, whilst these methods are in general suitable for many purposes, we have appreciated that they are characterized by wide particle size distributions, poor precision and limited reproducibility.

Conceptually, a particle processing method which would achieve a monodisperse distribution, that is, particles all having the same dimension in the desired attribute (size, shape or mass) would meet the desired requirements, but known methods are in fact poor at achieving such desired uniformity, precision and reproducibility.

In fact, monodisperse particles or particles approximating monodispersion are extremely interesting for pharmaceutical drug delivery. One of the most important features of monodisperse particles is that the physical and chemical characteristics of a single particle can be extrapolated to the whole particle population [T. Sugimoto, Monodispersed Particles, Elsevier 2001]. This facilitates the physical delivery of the drug to the human body and the prediction of the drug bioavailability upon delivery of the dosage form. In the case of oral dosage forms, monodisperse particles allow for a more predictable dissolution profile. In the case of IV injectable administration, the size of the drug particles dictates their distribution in the target tissue (if particles are too small, they may be removed too rapidly from the blood stream; if they are too large, they can cause embolism or may be trapped and not reach the intended site of action). Inhalation powders can also benefit from monodisperse particles, as particles which are too large may impact the oropharynx and fail to reach the deep lung, whereas particles which are too small may be re-exhaled and not be retained in the bronchi or in the alveoli.

Another advantage of near monodisperse particles in the case of inhaled drug products, is that by choosing a very precise particle size, with a very narrow distribution, very specific lung regions may be targeted for deposition. Also, by mixing a drug product comprising two distinct size fractions, different areas of the lung may be targeted by the same product. Furthermore, the same reasoning may be applied to formulations comprising two or more drugs, which if having different size distributions, can each target a different area of the lung. Very precise manufacturing of drug particles would allow the manufacture of hitherto impossible to manufacture pharmaceutical drugs, particularly in the area of pulmonary inhalation.

Conventional wet milling particle size reduction methods include, among others, media milling and high pressure homogenization. However, the prior art does not offer the required precision or robustness of process. In the prior art, many such descriptions have been offered, without solving the problem of high particle size precision and reproducibility.

Keck et al. [C. M. Keck, R. H. Muller, Drug nanocrystals of poorly soluble drugs produced by high pressure homogenization, European Journal of Pharmaceutics and Biopharmaceutics 62 (2006) 3-16] disclose a method for the production of nanocrystals by high pressure homogenization in water-free media and water mixtures. Under such conditions, cavitation is minimized and small and stable nanocrystals are produced. There is also disclosed a method for the production of nanocrystals by combination of precipitation and homogenization. Homogenization provides for a high energy step that preserves a specific size range of the particles after precipitation. Hirokawa et al. in EP2143423A1 disclose a method for the production of pulverized particles of a crystalline organic compound by wet milling by mixing with a salt and a polyol. Average diameter of the particles obtained is 600 nm or less. These particles can then be applied for oral, injectable or inhalation administration.

However, the processes described by Keck et al. and Hirokawa et al. could not manipulate particle size and its distribution beyond the limits of high pressure homogenization and therefore are still characterized by the inherent limitations of these processes with respect to precision and reproducibility.

Dalziel et al. in WO2005/053851A1 disclose a method for particle size reduction using a high pressure media milling system. The method comprises as well a product collection/separation step to remove the solvent and totally recover the milled particles. Such product collection/separation step may comprise filtration and spray drying (among others known in the art).

However, the purpose of the collection/separation step is to isolate the particles from the fluid and not to classify them while recycling those that did not meet the size criteria.

Consequently, the particle size distribution of the final product is still dictated and limited by the milling step.

Kesisoglou et al. [F. Kesisoglou, S. Panmai, Y. Wu, Nanosizing—Oral formulation development and biopharmaceutical evaluation, Advanced Drug Delivery Reviews 59 (2007) 631-644] disclose a method for particle size reduction of APIs to the sub-micron range with ball milling or high pressure homogenization. Isolation of the final product can be accomplished with the use of spray drying.

Again, isolation of the final product by a drying process does not confer on the process any further classification step and the particle size distribution of the isolated material is therefore essentially dictated and limited by the milling step.

We have appreciated that there is therefore a need for a new process which will achieve a very high degree of precision and reproducibility in achieving or in approximating monodisperse particle size distributions.

A measure of distribution is the span. The span is obtained by measuring the size of particles using a known method, such as microscopy or laser diffraction, and determining the upper size limit of particles which make up 90%, 50% and 10% of the sample of particles and they are referred to as D90, D50 and D10. The span is equal to (D90−D10)/D50. D50 is also referred to as the median particle size.

A perfect monodisperse distribution would have a span of zero, as D90, D50 and D10 would be the same. Currently, most milling methods result in spans between 1.5 and 3. Certain techniques are already able to achieve spans close to 1, but there is still room for improvement. We have now developed a process which enables this improvement by significantly and predictably reducing particle size distribution spans and this represents a considerable advance in the field.

The present invention relates to a method for the production of monodisperse or near monodisperse particles comprising the steps of milling and membrane separation.

According to one aspect of the present invention, there is provided a method for producing particles, particularly particles having a reduced particle size distribution, which method comprises the steps of:
 a) providing a composition comprising particles;
 b) subjecting the particles in said composition to a size reduction step or to a size growth step;
 c) feeding said particles to a first membrane separation system to separate said particles according to size;
 d) recycling those particles that do not meet the size criteria back to step a);
 e) optionally, collecting in a collection tank the permeate of the first membrane separation system.

In step d), the recycling may be done directly back to step b), depending upon the arrangement.

The method can be used to produce monodisperse particles, or particles which are essentially or near monodisperse, and compositions comprising such particles.

Preferably, the composition is a pharmaceutical composition comprising particles of a drug (i.e. an API), or particles of chemical intermediates of drugs, although it will be appreciated that the process can in principle be applied to any type of particle.

In a preferred aspect, the composition comprises a suspension of the particle or drug in a solvent. Any suitable solvent may be used.

Preferably, the first membrane separation system comprises a membrane filtration system, although any suitable membrane separation system may be used.

In a preferred aspect of the invention, the particle size is reduced. Whilst any suitable size reduction method may be used, it is preferred to use milling, more preferably wet milling.

If desired, the method of the invention may further comprise, after step e), the step of feeding a second membrane separation system. This may, for example, be used for removal of solvent and/or removal of particles below or above a selected target size. Preferably, it removes particles below a selected target size.

In a further aspect of the invention, there is provided a method for producing a pharmaceutical composition, particularly a composition comprising particles having a reduced particle size distribution, which process comprises the steps:
 i. forming a suspension comprising a drug and a solvent;
 ii. feeding said suspension to a wet mill (10) for reduction of the particle size of said suspension;
 iii. feeding said suspension to a first membrane filtration system (16) for separation of the particles;
 iv. recycling back to step i. those particles that do not meet the size criteria; and optionally;
 v. collecting in a collection tank (18) the permeate of the first membrane filtration system (16).

In step iv., the recycling may be done directly back to step ii), depending upon the arrangement. The invention also provides apparatus which is suitable for carrying out the process of the invention.

Thus, in a further aspect, the invention provides apparatus suitable for producing particles having a reduced particle size distribution, which apparatus comprises:
 a) means for providing a composition comprising particles;
 b) means for subjecting the particles in said composition to a size reduction step or to a size growth step;
 c) means comprising a first membrane separation system to separate said particles according to size;
 d) means for recycling those particles that do not meet the size criteria back to step a);
 e) optionally, means for collecting the permeate of the first membrane separation system.

Preferably, step (iv) recycles the particles to a feed tank (12) which feeds said wet mill (10).

The method of the invention may comprise, after step v., the step of feeding a second membrane filtration system (22) for removal of the solvent and/or removal of particles below a selected target size.

The invention also provides particles which are obtained, or are obtainable, according to the method of the invention. Such particles are characterized by having a monodisperse, or near monodisperse, particle size distribution. Preferably the particle is a drug (i.e. API) or an intermediate compound therefor.

Particles with a monodisperse particle size distribution are suitably those which have a span value of equal to, or less than, about 2. Accordingly, particles characterized by having a particle size distribution with a span of less than 2, or 2.0, are particularly preferred.

The invention also provides particles characterized by having a particle size distribution with a span of equal to, or less than about 1.5; or equal to, or less than, 1 or 1.0. Particles, especially API particles, having a particle size distribution with a span of less than 1.0 are also particularly preferred.

The invention also provides a pharmaceutical composition comprising particles according to the invention. The composition may comprise one or more pharmaceutically acceptable excipients, as will be clear to the skilled person. Injectable, inhalation, or oral formulations are preferred, and also formulations suitable for other topical routes of administration may be used, as desired by the skilled person according to need.

The invention thus also provides the use of particles obtained by a method according to the invention for the manufacture of injectable, inhalation, or oral formulations or for formulations suitable for other topical routes of administration.

The invention also provides a pharmaceutical composition comprising particles according to the invention, for use as a medicament.

Preferably, the milling step comprises high pressure homogenization of the product particles in suspension, or another suitable process. The membrane separation process operates in parallel or in series to the milling process, enabling the separation of particles smaller than a pre-defined size from the mill feed tank. Those particles smaller than a pre-defined size separated within the membrane separation process are collected in a permeate tank. Larger particles are re-circulated back into the milling step of the process, so that only the desired particles are obtained. The particles which are collected in the permeate tank are characterized by having a particle size distribution that is narrower than the starting material but also than that of the milled material, i.e., the particles in the permeate have a smaller span. This smaller span is achieved by recirculation of the milled material and its size characteristics are dictated by the pore size of the selected membrane.

It should be noted that while this process is essentially directed at the precise size reduction of particles, it can also be used for the precise size growth of particles, by using a starting process which instead of reducing particles, grows them through crystallization or some other process. The key step is the recirculation of the processed particles through a separation mechanism which collects them only when they are comprised within the desired physical limits. Failing to comply with these limits redirects the particles back to the size reduction or size growth step.

In the case of size reduction, a high pressure homogenizer apparatus or other liquid based system will be built with a membrane-based classification system, and such a construction is new.

The invention thus also provides a system for producing particles having a reduced particle size distribution, which system comprises a high pressure homogenizer apparatus and a membrane-based separation system. The membrane-based separation system is preferably a membrane-based filtration system.

Combining milling and membrane filtration provides for particle size adjustment and classification according to particle size. However, the current invention, which also includes the recycling of larger particles to the milling stage, enables a surprising level of control over target particle size and particle size distribution. This cannot be attained by any of the isolated processes nor by their combination, without a recycling step.

The present process can thus be used to produce a pharmaceutical composition comprising the steps of forming a suspension comprising a drug and a solvent, where the solvent may be an anti-solvent such that the drug or excipient is suspended; and feeding said suspension to a wet mill for the reduction of the particle size of the suspended particles; and feeding said suspension to a first membrane filtration system for the separation of the particles with the required size; recycling back to the feed tank those particles that do not meet the size criteria and optionally collecting in the collection tank the permeate of the membrane filtration for removal of the solvent and/or removal of particles below a given target size. This process is new.

The method of the invention may comprise feeding of the particles or suspension comprising said particles to the membrane separation system in parallel with the step of subjecting the particles to said size reduction step or said size growth step.

Alternatively, the method of the invention may comprise feeding of the particles or suspension comprising said particles to the membrane separation system in series with the step of subjecting the particles to said size reduction step or said size growth step.

For example, in the methods of the invention, the feeding of the composition or suspension from, for example, the feed tank to the first membrane filtration may be made in parallel or in series to the wet mill. Also, the feeding of the suspension to the wet mill and hence to the first membrane filtration may be made sequentially or simultaneously.

The method of the invention may further comprise the steps of recycling the retentate of the first membrane system to the feed tank and recycling the milled suspension from the wet mill to the feed tank.

The method of the invention may further comprise the step of feeding the milled suspension from the wet mill to the first membrane system and recycling the retentate of the membrane system to the feed tank.

The method of the invention may further comprise the step of feeding the suspension from the first membrane system to the wet mill and recycling the milled suspension from the wet mill to the feed tank.

The method of the invention may further comprise the feeding of the permeate suspension of the first membrane system to a second membrane system, recycling the retentate of the second membrane system to a collection tank, and recycling the permeate of the second membrane system to the feed tank.

The method of the invention may further comprise the feeding of make-up solvent to the feed tank.

The method of the invention may further comprise the isolation of the solid particles from the processed suspension obtained in the permeate of the first membrane system.

The method of the invention may further comprise an isolation step comprising spray drying, filtration or centrifugation.

In the method of the invention, the wet mill can be of any suitable type; for example of the media milling type or of the high-pressure homogenization type.

In the method of the invention, the composition or suspension can be comprised of one solvent, or a mixture of solvents including water and/or an organic solvent or solvents.

In the method of the invention, the feed mixture may comprise in addition to the drug substance surfactants, polymers or other components known in the art, either dissolved, emulsified or suspended, with the aim of aiding the process or improving the formulation.

In the present method, the membrane module in both membrane filtration systems can be of the flat sheet type, tubular, spiral or hollow fiber.

In the present method, the membrane in both membrane filtration systems can be of inorganic microsieve type or polymeric track-etched.

In the present method, the particles collected in the permeate of the first membrane system are preferably characterized by having a particle size distribution narrower than the milled particles and the span of the particle size distribution can be smaller than 2 or 2.0, 1.5 or 1 or 1.0.

In the present method, the pore size of the membrane in both membrane systems may range between 1 nm and 100 µm.

The particles obtained via the present invention suitably have a distribution approximating a monodisperse size distribution and their span obtained via this method may be less than 2.0 or 1.5 or 1.0.

The particles obtained via the above method may be used to manufacture injectable, topical, inhalation or oral formulations.

Such methods and particles obtained via such methods, and uses of such particles are novel.

Preferably, the apparatus of the invention is such that:
a) the means for providing a composition comprising particles comprises a feed tank (12);
b) the means for subjecting the particles in said composition to a size reduction step or to a size growth step, comprises a wet mill (10);
c) the first membrane separation system to separate said particles according to size comprises a first membrane filtration system (16);
and wherein
e) the means for collecting the permeate of the first membrane separation system comprises a collection tank (18).

The means d) for recycling those particles that do not meet the size criteria back to step a) (or directly to step b) if desired) may be any suitable means, such as a suitable conduit or pipe (equipped if necessary with a pump), as will be clear to the skilled person, provided it functions to deliver the recycled composition or suspension back to the desired part of the apparatus.

The apparatus of the invention may comprise, or further comprise, any of the features referred to above in the context of the method, which features give effect to the process of the invention.

For instance, the apparatus of the invention may further comprise a second membrane separation system for removal of solvent and/or removal of particles below or above a selected target size, after collection of said permeate.

Preferably, in the apparatus, the means for recycling the particles recycles the particles to a feed tank (12) which feeds the said wet mill (10).

The apparatus may, if desired, be configured such that feeding of the composition or suspension from the feed tank (12) to the membrane filtration system (16) is made in parallel to the wet mill (10).

Alternatively, the apparatus may be configured such that feeding of the composition from the feed tank (12) to the membrane filtration system (16) is made in series to the wet mill (10).

In a further aspect, the apparatus may be configured such that feeding said composition to said wet mill (10) for reduction of the particle size of said suspension; and feeding said composition to said first membrane filtration system (16) for separation of the particles; occur sequentially or simultaneously.

The apparatus may be configured such that the retentate of the first membrane filtration system (16) is recycled to a feed tank (12) and such that the milled suspension from the wet mill (10) is recycled to a feed tank (12).

In the apparatus, a wet mill (10) is preferably used, and this is preferably of the media milling type or of the high-pressure homogenization type.

In the apparatus, preferably the membrane module in either or both of the first and the second membrane separation systems is of the flat sheet type, tubular, spiral or hollow fiber.

In the apparatus, preferably the membrane in either or both of the first and the second membrane separation systems is a inorganic microsieve type or is polymeric track-etched.

Figure 1:
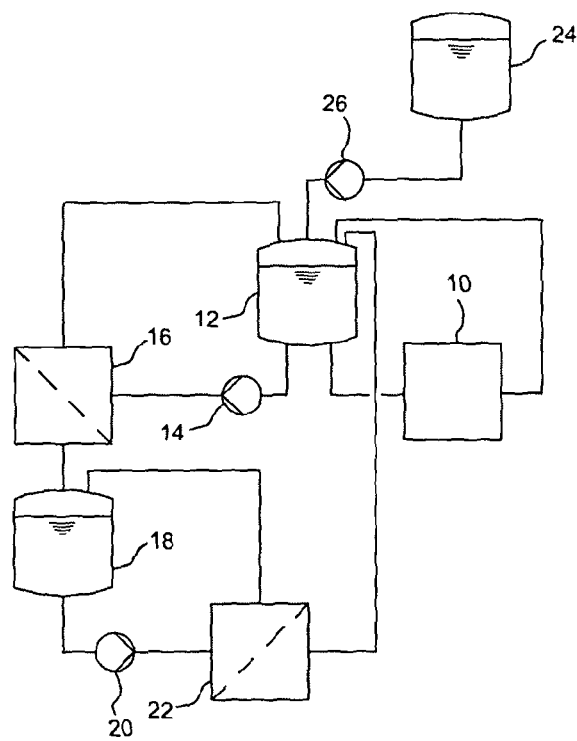
FIG. 1 and FIG. 2 illustrate particular embodiments of the process of the present invention with a wet mill and membrane system operating in parallel and in series, respectively.

Referring now to the invention in more detail, in FIG. 1 it is shown a wet mill 10 that is fed by a suspension from tank 12 and the milled suspension is afterwards recycled back to tank 12. Tank 12 also feeds a pump 14 that transports the suspension through a first membrane filtration system 16 and recycles it back to tank 12. The permeate suspension from the first membrane filtration system 16 is collected in a tank 18. The suspension from tank 18 feeds a pump 20 that transports the suspension through a second membrane filtration system 22 and recycles it back to tank 18. The permeate stream from the second membrane filtration system 22 is recycled to tank 12. An additional tank 24 can feed make-up solvent if needed to tank 12 through a pump 26.

In more detail, still referring to the invention of FIG. 1, the particle size reduction rate in the wet mill 10 can be adjusted depending on selected operating conditions. The pressure in both the retentate and permeate compartments of the membrane filtration system 16 and 22 can be adjusted to meet the desired separation efficiency. The flow rate and pressure in the membrane filtration system 16 can be adjusted depending on the particle size reduction rate in the wet mill 10. With an adequate set of operating conditions of the combined process, the suspension in tank 12 will be continuously depleted from those particles that are smaller than a pre-defined size, which in turn will be continuously collected in tank 18. Hence, the suspension collected in tank 18 will possess a particle size distribution approximating a monodisperse distribution and will have a particle size that is dictated by the pore size of the selected membrane.

In further detail, still referring to the invention of FIG. 1, the wet mill 10 can, for example, be of the media milling type or of the high-pressure homogenization type. The suspension in tank 12 can be comprised of one solvent, or a mixture of solvents. The solvent in the suspension in tank 12 can, for example, be water and/or one or more organic solvents. Within the feed mixture there may be in addition to the drug substance other components, either dissolved, emulsified or suspended, with the aim of aiding the process or improving the formulation. The membrane module in the membrane filtration systems 16 and 22 can be of the flat sheet type, tubular, spiral or hollow fiber. The membrane in the membrane filtration system 16 is selected based upon the target particle size to be achieved for the final near monodisperse suspension in tank 18. Therefore, the membrane selected in 16 should allow for the permeation of particles having a desired pre-defined size. The membrane type to be selected in 16 and 22 is preferentially an inorganic microsieve, a polymeric track-etched or other suitable membrane that is characterized by a narrow pore size distribution. The membrane in the membrane filtration system 22 is selected for allowing the permeation of particles in tank 18 of a target size, and additionally for allowing the solvent to permeate and to be recycled back to tank 12.

Figure 2:
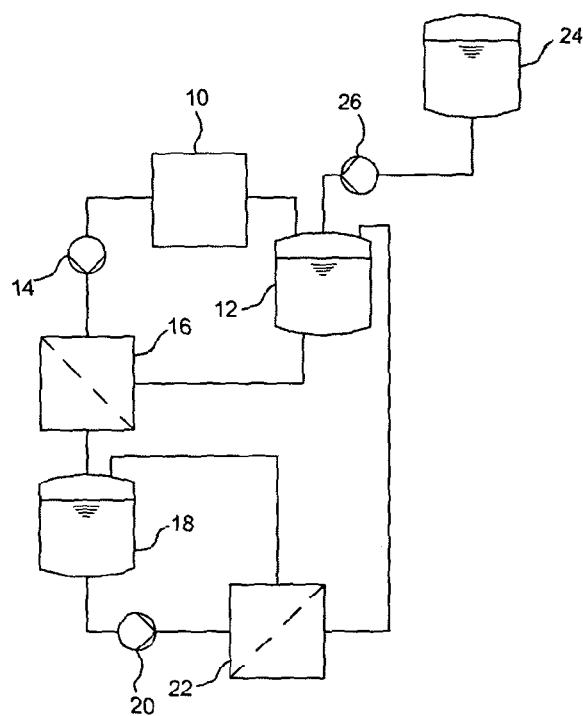

FIG. 2 shows the same system as in FIG. 1 where the feeding to the membrane filtration system 16 is done in series with the wet mill 10.

The advantages of the present invention include, without limitation, that it enables the production of near monodisperse particles from starting drug suspensions having a large span value. Such near monodisperse particles can then be post-processed depending on the delivery platform envisaged. In the case of injectable drug delivery, the near monodisperse suspension can be used without further processing, provided the required sterile operation criteria are met. For oral and inhalation drug delivery, the near monodisperse suspension can be isolated through an adequate process such as spray drying, filtration or centrifugation.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

EXAMPLES

Example 1

A 5% (w/w) suspension of drug A in water was processed in a cross-flow microfiltration system. An hydrophilic flat sheet track-etched polycarbonate membrane was used, with a pore size of 30 μm. The critical flux was determined by running experiments at different pressure values. Afterwards, the experiments were conducted below the critical flux conditions to minimize cake buildup in the membrane surface and to enhance the process selectivity. Particle size was analyzed by microscopy. The feed suspension had a span of 1.1 (D10=30 μm, D50=85 μm and D90=125 μm). After processing, the permeate had a span of 0.7 (D10=17 μm, D50=34 μm and D90=42 μm), i.e. a reduction in median particle size of 60% and in span of 34%. Moreover, the results show that the selected membrane was capable of efficiently classifying the feed suspension to particle sizes that are dependent on the selected membrane pore size.

Example 2

A 10% (w/w) suspension of drug A in water was milled using a high-pressure homogenizer. The milled suspension was analyzed by microscopy, having a span of 1.0 (D10=2.8 μm, D50=4.8 μm and D90=7.5 μm). The milled suspension was then processed by membrane filtration using track-etched membranes in two different tests. In the first test, a 1 μm pore size membrane was used. The permeate suspension from the first test showed particles with a span of 0.7 (D10=1.5 μm, D50=2.1 μm and D90=2.9 μm), i.e. a reduction in median particle size of 56% and in span of 32%. In the second test, the same milled suspension was processed using a 3 μm pore size membrane. In this case the permeate suspension showed particles with a span of 0.7 (D10=1.8 μm, D50=2.6 μm and D90=3.7 μm), i.e. a reduction in median particle size of 46% (therefore not as pronounced, because of the larger pore size) and in span of 25%. Moreover, the results show that the selected membranes were capable of efficiently classifying the feed suspension to particle sizes that are dependent on the selected membrane pore size. The only difference in the two tests was the use of membranes of different pore sizes, which clearly demonstrates the role the classification system plays.

Example 3

A 5% (w/w) suspension of drug A in water (700 mL) was processed sequentially by a high pressure homogenizer and a cross-flow microfiltration system, with the membrane separation step being conducted in between each cycle of the homogenization process. A hydrophilic flat sheet track-etched polycarbonate membrane was used, with a pore size of 30 μm. The permeate from the first membrane filtration system was further processed by a 3 μm track-etched polycarbonate membrane to concentrate the particles and remove the solvent. Water was continuously added to the feed tank to maintain the feed volume constant. The homogenizer was operated at a pressure of 500 bar using a 200 μm chamber for the first 6 cycles, and 200 and 100 μm chambers in series for the subsequent cycles. Particle size of the feed suspension was analyzed by laser diffraction. Particle size of the permeate samples was analyzed by microscopy given the very low concentration of suspended particles (low obscuration index by laser diffraction). The feed suspension had an initial D50 of 32 μm and a span of 1.9 (D10=5.6 μm, D50=32.0 μm and D90=67.2 μm). The D50 in the feed tank evolved as follows with the number of cycles: cycle 1—10.4 μm; cycle 2—10.1 μm; cycle 3—6.9 μm; and cycle 8—3.8 μm. After 8 cycles, the feed suspension had a span of 1.6 (D10=1.7 μm, D50=3.8 μm and D90=7.9 μm). Microscopy analysis of the permeate suspension after 8 cycles showed particles with a span of 0.9 (D10=4.2 μm, D50=6.5 μm and D90=10.0 μm). The lower class, D10, did not show a marked reduction, but the median particle size was reduced five-fold and D90, more than six-fold. The span was reduced by more than half, by 54%. The example shows that the process can also be used to target preferentially certain parts of the distribution curve, while leaving others unchanged. In this case, the distribution curve when represented in a chart was significantly moved to the left, but its left-most portion was not substantially modified.

In summary,

| Example | D10 (μm) | D50(μm) | D90 (μm) | Span |
| --- | --- | --- | --- | --- |
| Example 1 feed | 30.0 | 85.0 | 125.0 | 1.1 |
| Example 1 final | 17.0 | 34.0 | 42.0 | 0.7 |
| Example 2a feed | 2.8 | 4.8 | 7.5 | 1.0 |
| Example 2a final | 1.5 | 2.1 | 2.9 | 0.7 |
| Example 2b feed | 2.8 | 4.8 | 7.5 | 1.0 |
| Example 2b final | 1.8 | 2.6 | 3.7 | 0.7 |
| Example 3 feed | 5.6 | 32.0 | 67.2 | 1.9 |
| Example 3 final | 4.2 | 6.5 | 10.0 | 0.9 |

These four experiments also demonstrate that the final span is independent of the particle size dimension; whereas the final spans of the samples in the fine class (examples 1 and 2, D50s of 2.1 to 6.5 μm) is around 0.7, the final span of the coarser product sample (example 3), 0.9, is of the same order of magnitude.

The invention claimed is:
1. A method for producing particles of active pharmaceutical ingredients, drug product intermediates, excipients or drug products having a reduced particle size distribution, which method comprises the steps of:

a) providing a composition comprising a suspension of particles of active pharmaceutical ingredients (APIs), drug product intermediates, excipients or drug products in a solvent;
b) subjecting the particles in said composition to a size reduction step or to a size growth step;
c) feeding said particles to a first membrane separation system to separate said particles according to size by feeding said particles to a first membrane separation system in parallel with the step b) of subjecting said particles to a size reduction step or to a size growth step; and
d) recycling those particles that do not meet the size criteria back to step a.

2. A method according to claim 1 wherein the method further comprises the step of:
e) collecting in a collection tank the permeate of the first membrane separation system.

3. A method according to claim 1, wherein the composition is a pharmaceutical composition comprising particles of a drug.

4. A method according to claim 1, wherein the first membrane separation system comprises a membrane filtration system.

5. A method according to claim 1, wherein the particle size is reduced by milling.

6. A method according to claim 2, further comprising, after step e), the step of feeding a second membrane separation system for removal of solvent and/or removal of particles below or above a selected target size.

7. A method according to 1, for producing a pharmaceutical composition comprising the steps:
 i. forming a suspension comprising a drug and a solvent;
 ii. feeding said suspension to a wet mill for reduction of the particle size of said suspension;
 iii. feeding said suspension to a first membrane filtration system for separation of the particles; and
 iv. recycling back to step (i) those particles that do not meet the size criteria;
 wherein the feeding of the suspension from the feed tank to the membrane filtration system is made in parallel to the wet mill.

8. A method according to claim 7 wherein the method further comprises the step of:
 v. collecting in a collection tank the permeate of the first membrane filtration system.

9. A method according to claim 7 wherein step (iv) recycles the particles to a feed tank which feeds said wet mill.

10. A method according to claim 8 further comprising, after step (v), the step of feeding a second membrane filtration system for removal of the solvent and/or removal of particles below a selected target size.

11. A method according to g claim 1, wherein the feeding of the particles or suspension comprising said particles to the membrane separation is made in parallel to the step of subjecting the particles to said size reduction step or said size growth step.

12. A method according to claim 6, further comprising the steps of recycling the retentate of the first membrane filtration system to a feed tank and recycling the milled suspension from the wet mill to the feed tank.

13. A method according to claim 1, further comprising the feeding of the permeate particles or suspension comprising said particles to a second membrane separation system, recycling the retentate of the second membrane separation system to a collection tank, and recycling the permeate of the second membrane separation system to a feed tank.

14. A method according to claim 1, further comprising the feeding of make-up solvent to a feed tank.

15. A method according to claim 1, further comprising the isolation of solid particles from processed composition or suspension.

16. A method according to claim 15, wherein the isolation step comprises one or more of: spray drying, filtration or centrifugation.

17. A method according to claim 1, wherein a wet mill is used and is of the media milling type or of the high-pressure homogenization type.

18. A method according to claim 1, wherein a suspension of particles is used, and the suspension comprises one solvent, or a mixture of solvents.

19. A method according to claim 18, wherein the solvent comprises water, and/or an organic solvent.

20. A method according to claim 1, wherein the feed mixture comprises, in addition to a drug substance, surfactants; polymers; or other suitable components; either dissolved, emulsified or suspended in said mixture, with the function of aiding the process or improving the formulation.

21. A method according to claim 1, wherein the membrane in either or both first and second membrane separation systems is of the flat sheet type, tubular, spiral or hollow fiber.

22. A method according to claim 1, wherein the membrane in either or both first and second membrane separation systems is a inorganic microsieve type or is polymeric track-etched.

23. A method according to claim 1, wherein the span of the particle size distribution of the permeate composition or suspension is less than 2.0.

24. A method according to claim 23 wherein the span of the particle size distribution of the permeate composition or suspension is less than 1.5.

25. A method according to claim 24 wherein the span of the particle size distribution of the permeate composition or suspension is less than 1.0.

26. A method according to claim 1, wherein the pore size of the membrane in either or both first and second membrane separation systems ranges from 1 nm to 100 microns.

* * * * *

UNITED STATES PATENT AND TRADEMARK OFFICE
CERTIFICATE OF CORRECTION

PATENT NO. : 9,937,470 B2
APPLICATION NO. : 14/389117
DATED : April 10, 2018
INVENTOR(S) : Santos et al.

Page 1 of 1

It is certified that error appears in the above-identified patent and that said Letters Patent is hereby corrected as shown below:

In the Claims

Column 11, Claim 11, Line 54, after according to delete "g".

Signed and Sealed this
Fifth Day of June, 2018

Andrei Iancu
*Director of the United States Patent and Trademark Office*